United States Patent
Sekol et al.

(10) Patent No.: US 7,125,164 B2
(45) Date of Patent: Oct. 24, 2006

(54) DIGITAL RADIOGRAPHY APPARATUS

(75) Inventors: James W. Sekol, Rochester, NY (US); Ted G. Young, Rochester, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/994,762

(22) Filed: Nov. 22, 2004

(65) Prior Publication Data

US 2005/0226391 A1    Oct. 13, 2005

Related U.S. Application Data

(60) Provisional application No. 60/558,814, filed on Apr. 2, 2004.

(51) Int. Cl.
*G03B 42/02* (2006.01)
(52) U.S. Cl. .................................. 378/181; 378/167
(58) Field of Classification Search ................ 378/181, 378/102, 55, 170, 68, 195–198, 124, 16, 378/20, 167, 172–173, 177, 184, 204; 250/584, 250/587, 589, 580
See application file for complete search history.

(56) References Cited

U.S. PATENT DOCUMENTS

| 2,598,529 A | * | 5/1952 | Fritz ............................ 248/457 |
| 6,592,259 B1 | * | 7/2003 | Crain et al. .................. 378/197 |
| 6,754,306 B1 | * | 6/2004 | Cho et al. .................... 378/102 |
| 6,851,851 B1 | | 2/2005 | Smith et al. |
| 2004/0124379 A1 | * | 7/2004 | Yasuda ....................... 250/584 |

* cited by examiner

*Primary Examiner*—Edward J. Glick
*Assistant Examiner*—Hoon Song
(74) *Attorney, Agent, or Firm*—Susan L. Parulski

(57) ABSTRACT

A digital radiography apparatus. The apparatus includes a support member having a first axis; a bucky; and a mounting member attached to the support member and supporting the bucky. The mounting members is adapted to move the bucky substantially along a second axis perpendicular to the first axis between a retracted position wherein the bucky is disposed proximate the support member to an extended position wherein the bucky is not disposed proximate the support member.

14 Claims, 16 Drawing Sheets

DIGITAL RADIOGRAPHY APPARATUS

CROSS REFERENCE TO RELATED APPLICATION

Reference is made to, and priority is claimed from, provisional patent application U.S. Ser. No. 60/558,814 entitled "DIGITAL RADIOGRAPHY SYSTEM", filed on Apr. 2, 2004 in the name of Sekol, which is assigned to the assignee of this application, and incorporated herein by reference.

FIELD OF THE INVENTION

The invention relates to digital radiography, and in particular to a digital radiography system.

BACKGROUND OF THE INVENTION

Digital radiography systems are well known. In such digital radiography system, an x-ray source projects an x-ray beam through an object (such as a body part of an individual) to produce an x-ray image captured by a detecting member. The detector member can rely on direct conversion of x-rays to charge carriers or alternatively indirect conversion in which x-rays are converted to light which is then converted to charge carriers and charge readout.

The detector is typically mounted in a structure/member known as a bucky. The bucky can also house other elements, for example, but not limited to, an anti-scatter grid which is commonly used to prevent scattered radiation from affecting the final x-ray image. Such anti-scatter grids are typically employed when the object to be imaged is relatively thick (for example, a human chest).

The bucky can be mounted in various configurations, for example, on an x-ray table or on a radiographic stand, as shown in FIGS. 1A and 1B, respectively, wherein the bucky is element 5. However, the configurations shown in FIGS. 1A and 1B require a bucky for each mounting. That is, the bucky is mounted specifically for either a horizontal orientation (as shown in FIG. 1A) or for a vertical orientation (as shown in FIG. 1B).

There exists a need for a single bucky that could be disposed in a plurality of mounting configurations, including both horizontal and vertical orientations.

SUMMARY OF THE INVENTION

An object of the present invention is to provide an apparatus for positioning a bucky in a plurality of mounting configurations.

Another object of the present invention is to provide such an apparatus which can be used to position including both a horizontal and vertical orientation.

This object is given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a digital radiography apparatus. The apparatus includes a support member having a first axis; a bucky; and a mounting member attached to the support member and supporting the bucky. The mounting member is adapted to move the bucky substantially along a second axis perpendicular to the first axis between a retracted position wherein the bucky is disposed proximate the support member to an extended position wherein the bucky is not disposed proximate the support member.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
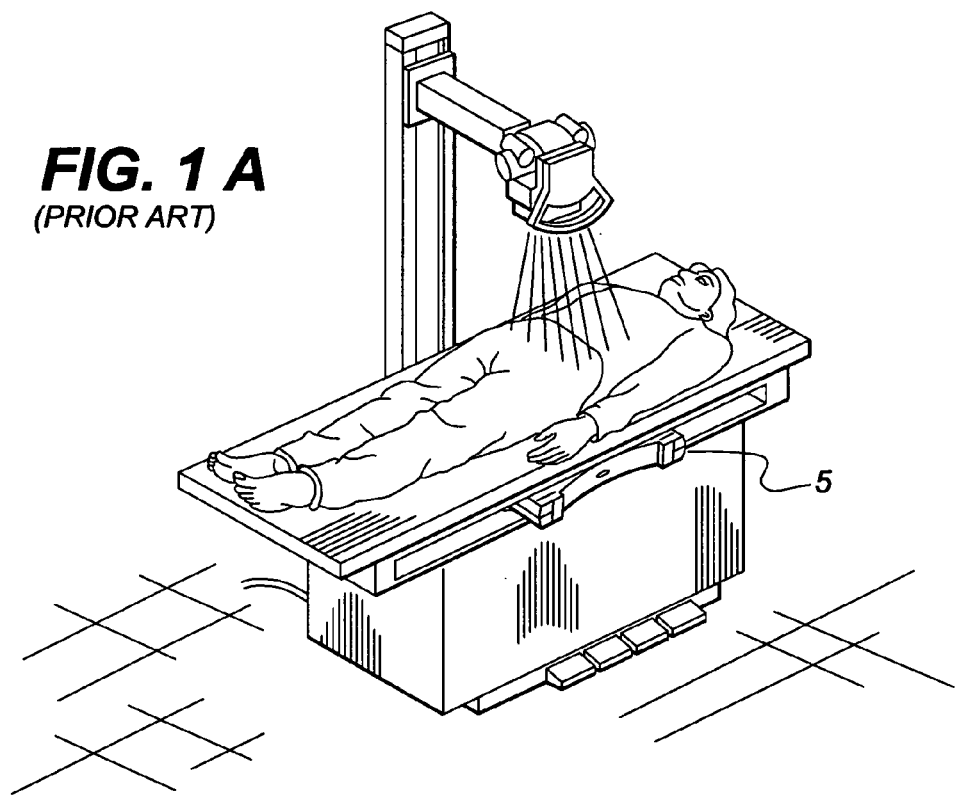
FIGS. 1A and 1B show prior art mounting configurations for a bucky.
Figure 1:
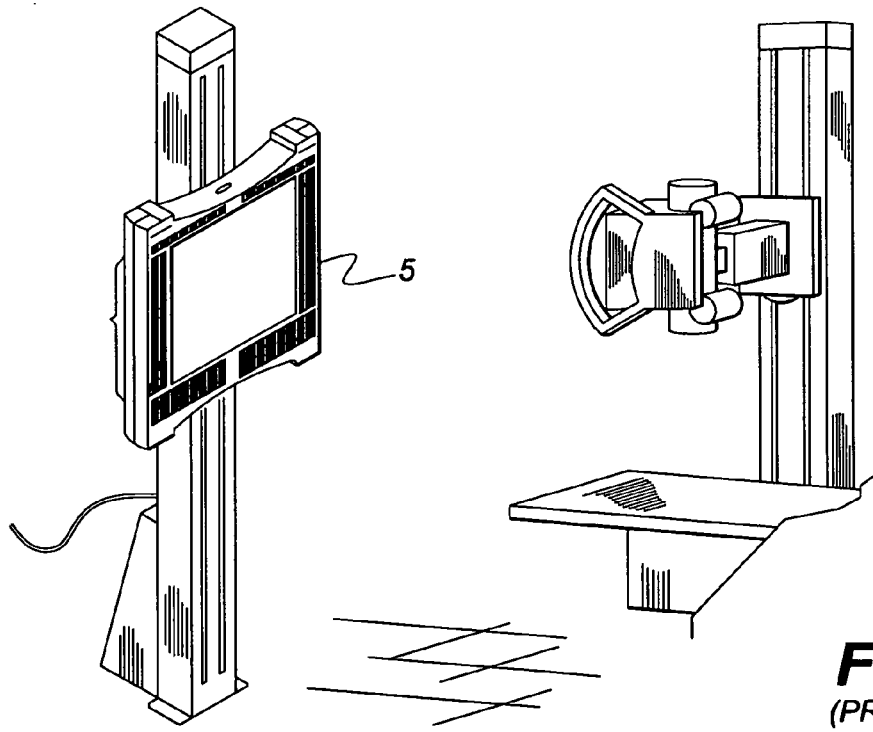

The following is a detailed description of the preferred embodiments of the invention, reference being made to the drawings in which the same reference numerals identify the same elements of structure in each of the several figures.

In a preferred arrangement, the present invention is a wall stand of a Digital Radiography (DR) system designed for x-ray image acquisition for both upright and horizontal projections. It uses an upright tilt bucky with an Overhead Tube Crane (OTC) to enable examinations such as chest, abdomen, pelvis, shoulder, standing knees, ankles and upper extremities (wrist, hand, forearm, and the like). The bucky tilt feature permits angled projections and imaging while the patient is on gurney. The wall stand that holds and supports the bucky provides novel method of implementing all of the required bucky motions.

Figure 4:
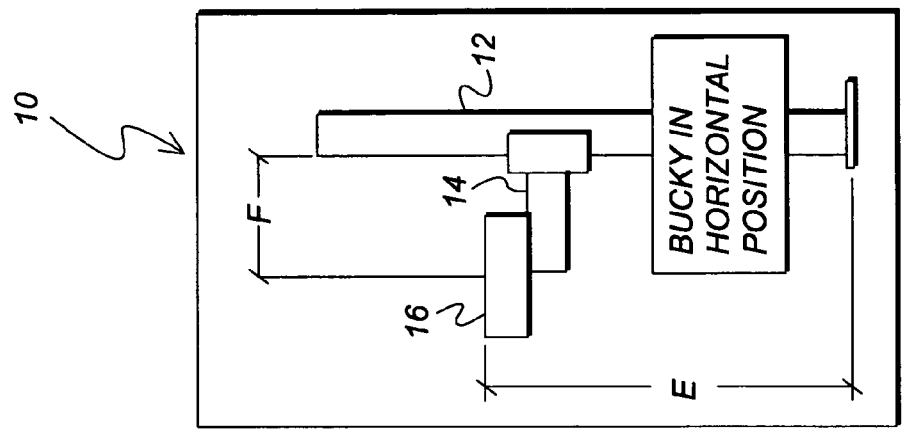
FIG. 4 shows the digital radiography apparatus of FIG. 2 wherein the bucky is in a horizontal position.
Figure 3:
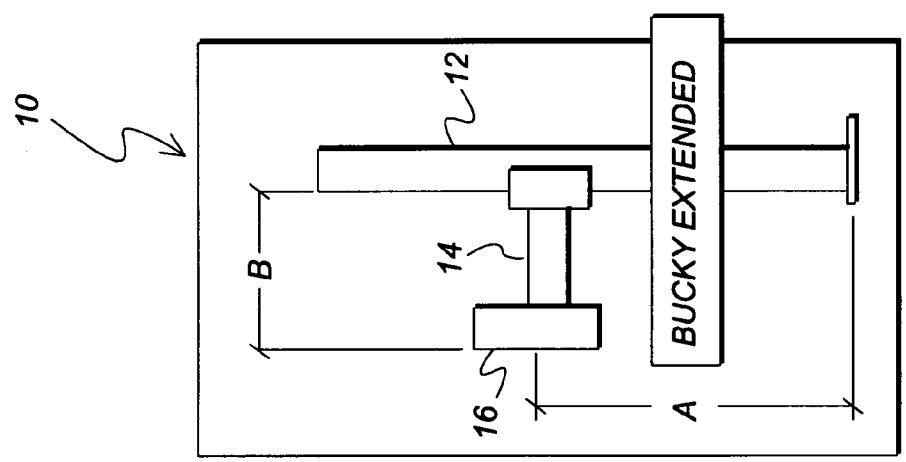
FIG. 3 shows the digital radiography apparatus of FIG. 2 wherein the bucky is in a fully extended vertical position.
Figure 2:
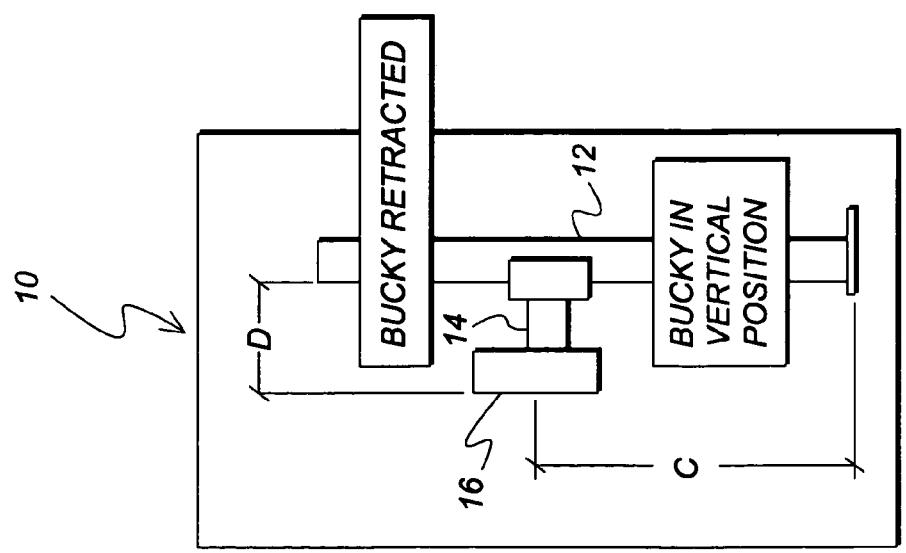
FIG. 2 shows a digital radiography apparatus in accordance with the present invention wherein the bucky is in a fully retracted vertical position.

The present invention is directed to a digital radiographic apparatus adapted to support a bucky. A first embodiment of the present invention is generally shown in FIGS. 2–4 as apparatus 10. As shown in these figures, apparatus 10 includes a support member 12 and a mounting member 14 adapted to mount/support a bucky 16.

Support member 12 is shown in the figures as a substantially vertical member. Support member 12 can be stationarily affixed to a base, such as a wall, floor, and/or ceiling. Alternatively, support member 12 can be mounted for translational/sliding movement in a direction substantially perpendicular to the axis of support member 12. Means to accomplish this translation/sliding movement are well known, for example, support member 12 can be mounted for movement along a rail (or rails) affixed to a wall, floor, or ceiling.

FIG. 2 shows mounting member 14 in a fully retracted position such that bucky 16 is in a fully retracted position and is disposed in a vertical orientation.

Mounting member 14 is configured to extend in a direction substantially perpendicular to the axis of support member 12 to extend bucky 16 away from support member 12. This position is shown in FIG. 3 wherein mounting member 14 is in a fully extended position, and bucky is disposed in a vertical orientation.

With mounting member 14 disposed in its fully extended position, bucky 16 can be rotated from its vertical orientation (as shown in FIGS. 2 and 3) to a horizontal position, as shown in FIG. 4. Means known to those skilled in the art can be disposed on mounting member 14 to affect such rotation of the bucky in this manner.

Figure 5:
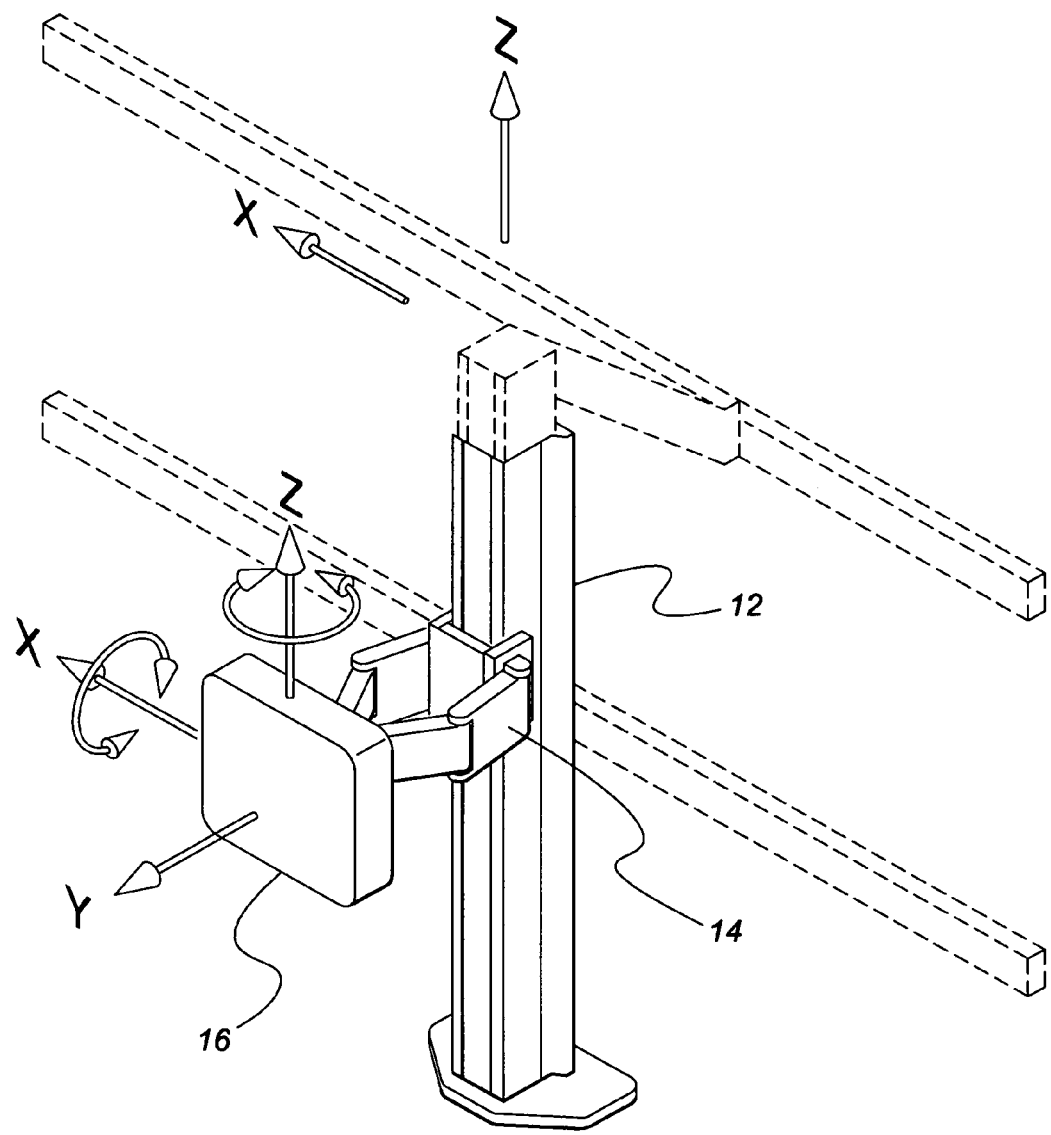
FIG. 5 shows a diagrammatic perspective view of the digital radiography apparatus wherein the bucky is in a partially extended vertical position.
Figure 6:
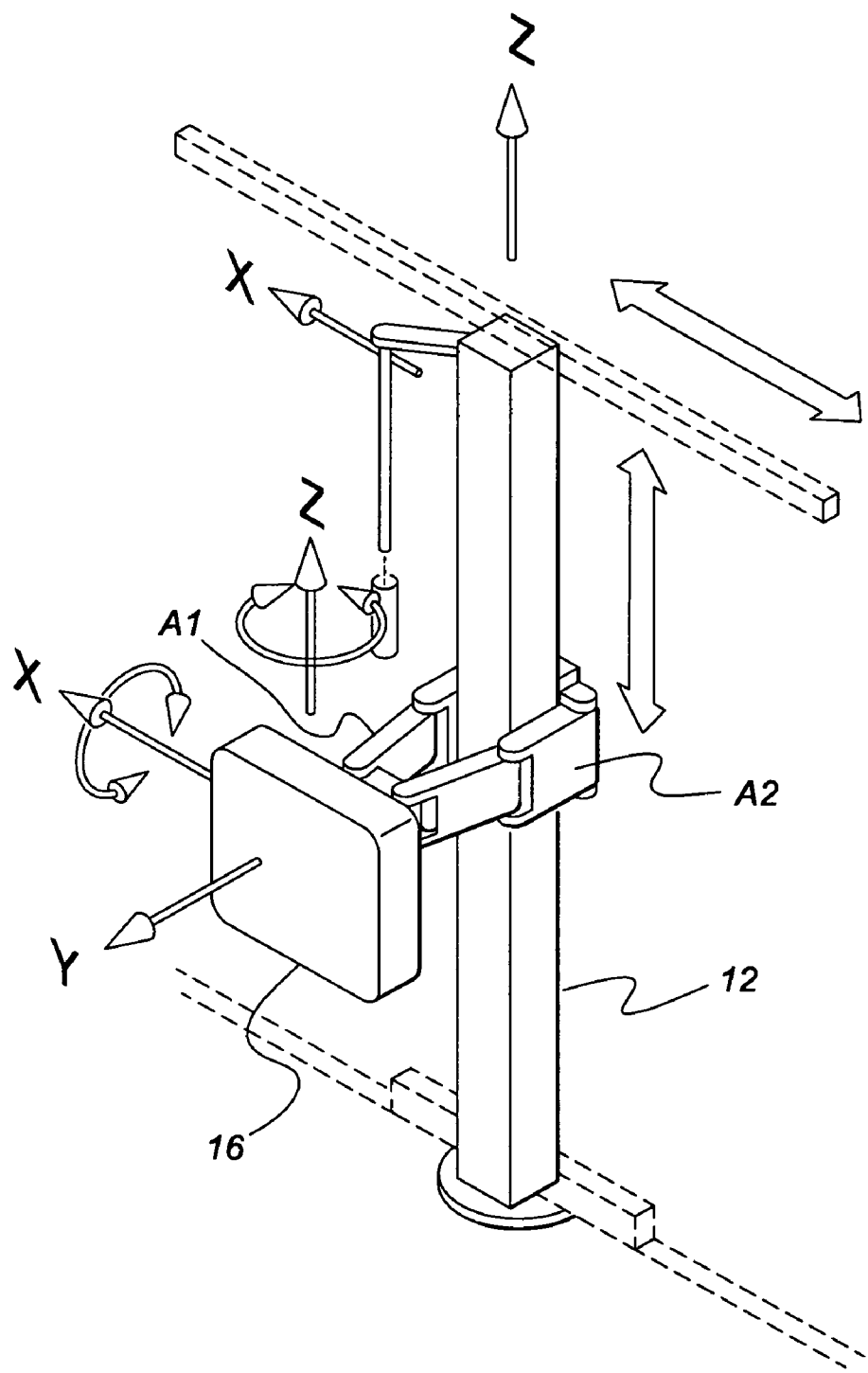
FIG. 6 shows a diagrammatic perspective view of the digital radiography apparatus wherein the bucky is in a fully extended vertical position.
Figure 7:
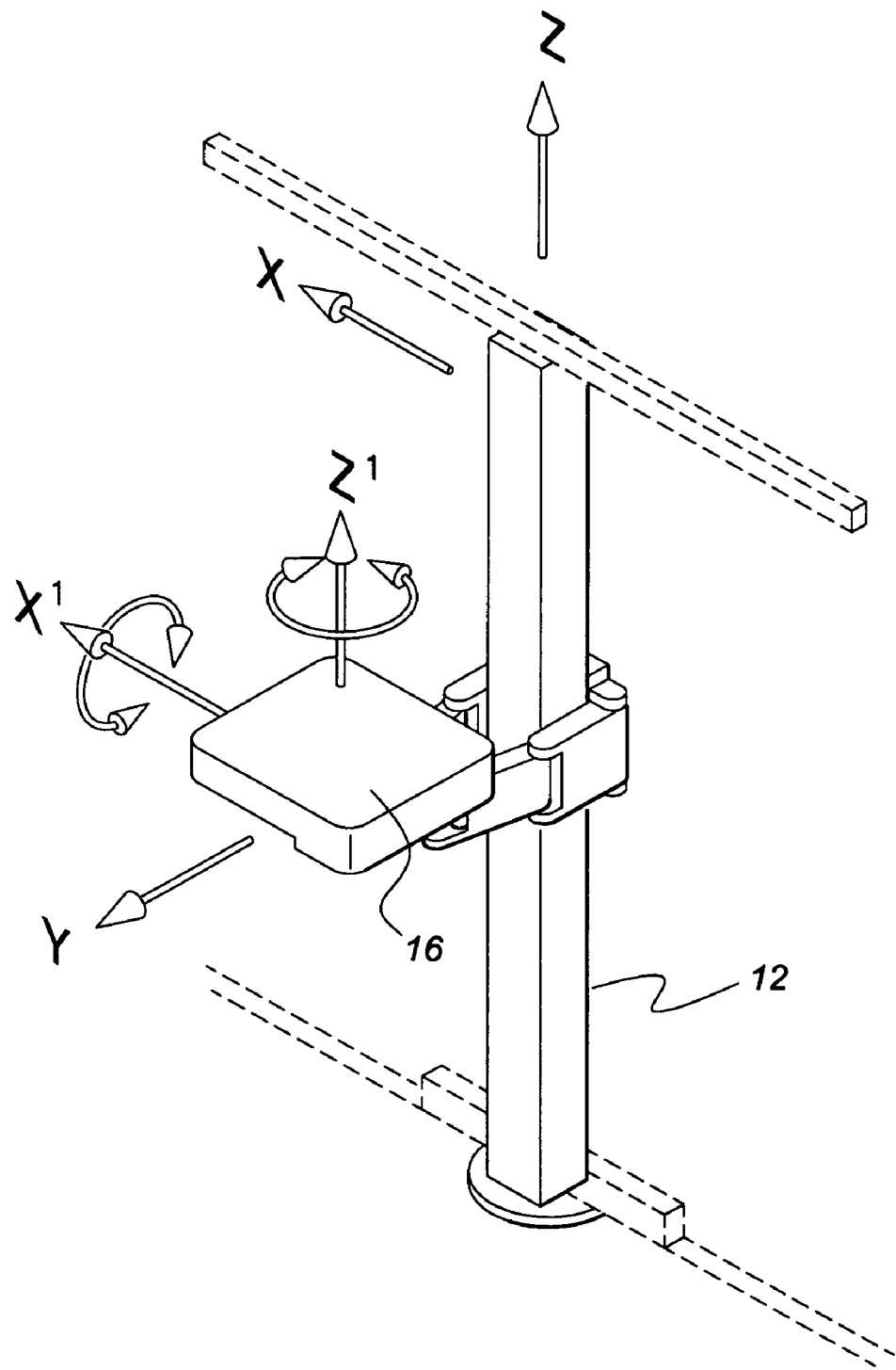
FIG. 7 shows a diagrammatic perspective view of the digital radiography apparatus wherein the bucky is in a horizontal position.

FIGS. 5–7 more particularly illustrated the support and movement of bucky 16. Bucky 16 has several degrees of freedom; the bucky can be extended, tilted, rotated, angulated and moved vertically.

As shown in the Figures, bucky 16 has movement in the z-direction. This is shown as vertical movement (up and down) in the figures.

Figure 8:
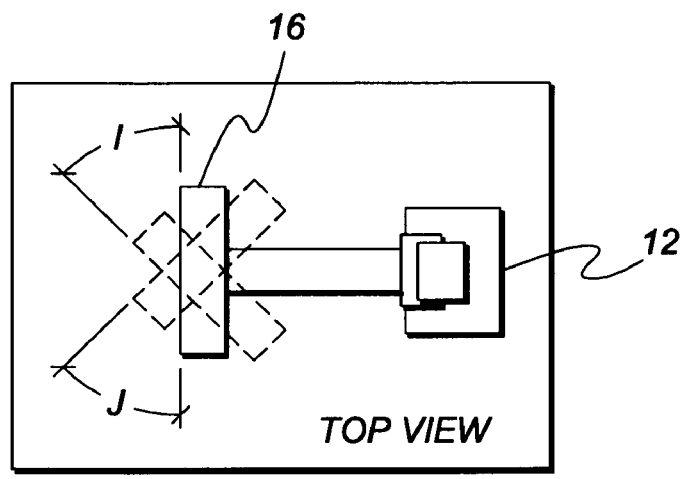
FIG. 8 shows a top view of the digital radiography apparatus illustrating the angulation feature of the bucky.

Bucky 16 further has angulation about the z-axis. That is, when bucky 16 is in the fully extended position, bucky 16 can pivot about the z-axis by an angular amount. This feature is more particularly described with reference to FIG. 8 which shows a top view of apparatus 10. This angular rotation can vary by +/−45 degrees from the z-axis.

Still further, bucky 16 can be moved between a retracted position and an extended position. In the retracted position, the bucky is disposed proximate support member 12. To move the bucky to the extended position, the bucky is moved along the y-axis from the retracted position in a direction away from support member 12 so as to not be proximate support member 12.

Yet still, when bucky 16 is in the extended position, bucky 16 can be rotated about the y-axis. This rotation may be desired if, for example, bucky 16 has a rectangular shape and it is desired to orient the bucky to capture as much of the anatomy as possible in a particular dimension. For example, it may be desired to capture an image in a landscape mode or a portrait mode. Means known to those skilled in the art can be disposed on mounting member 14 to affect such rotation of the bucky in this manner.

Figure 9:
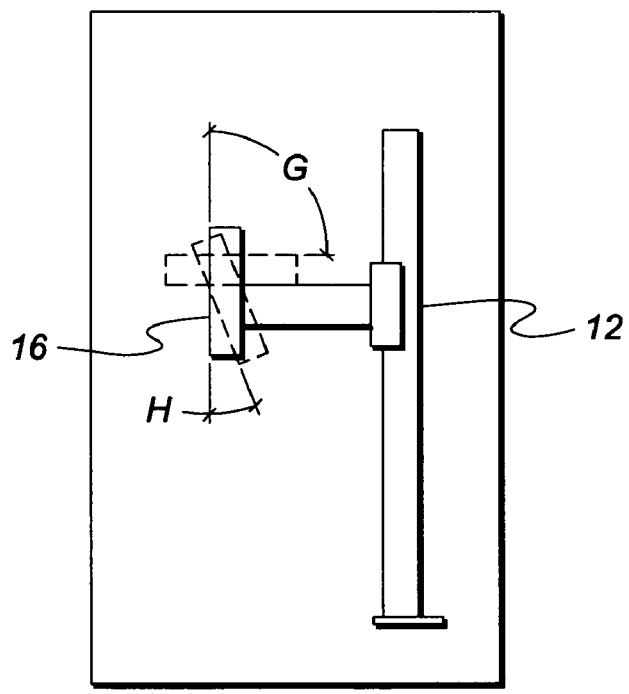
FIG. 9 shows a side view of the digital radiography apparatus illustrating the tilting of the bucky.
Figure 10:
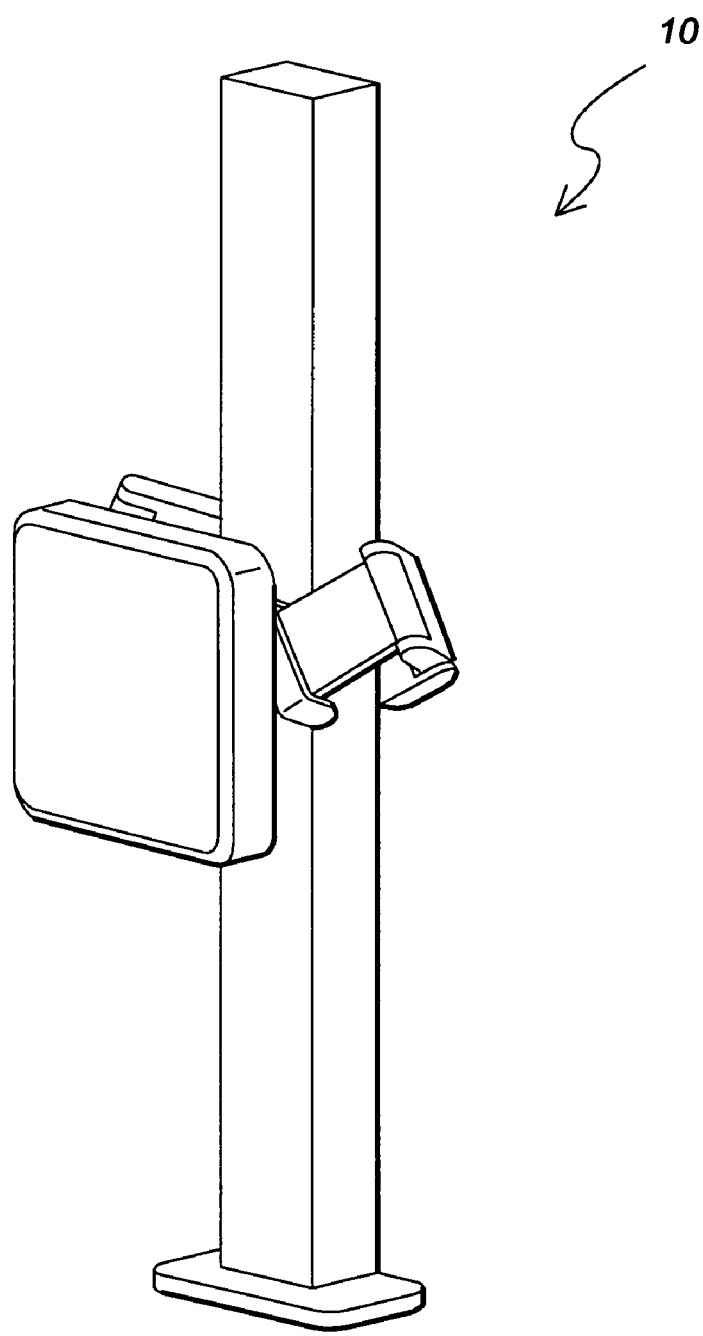
FIG. 10 shows a diagrammatic perspective view of the digital radiography apparatus wherein the bucky is in a retracted position.
Figure 11:
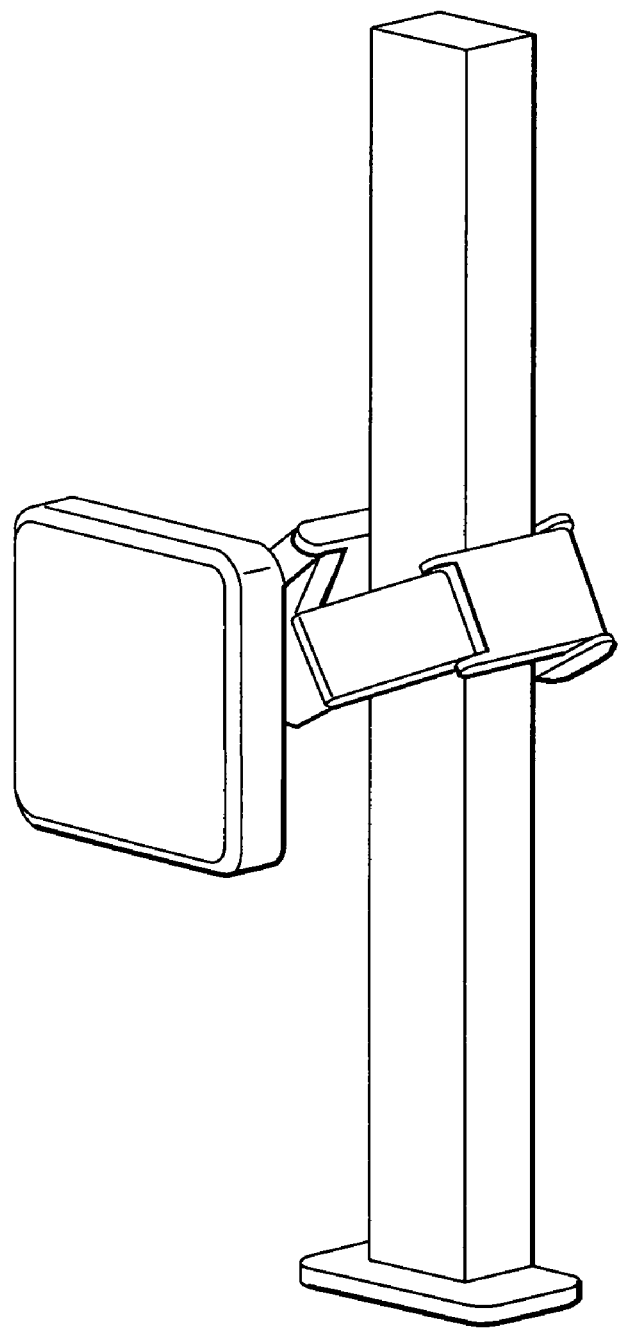
FIG. 11 shows a diagrammatic perspective view of the digital radiography apparatus wherein the bucky is in an extended position.
Figure 12:
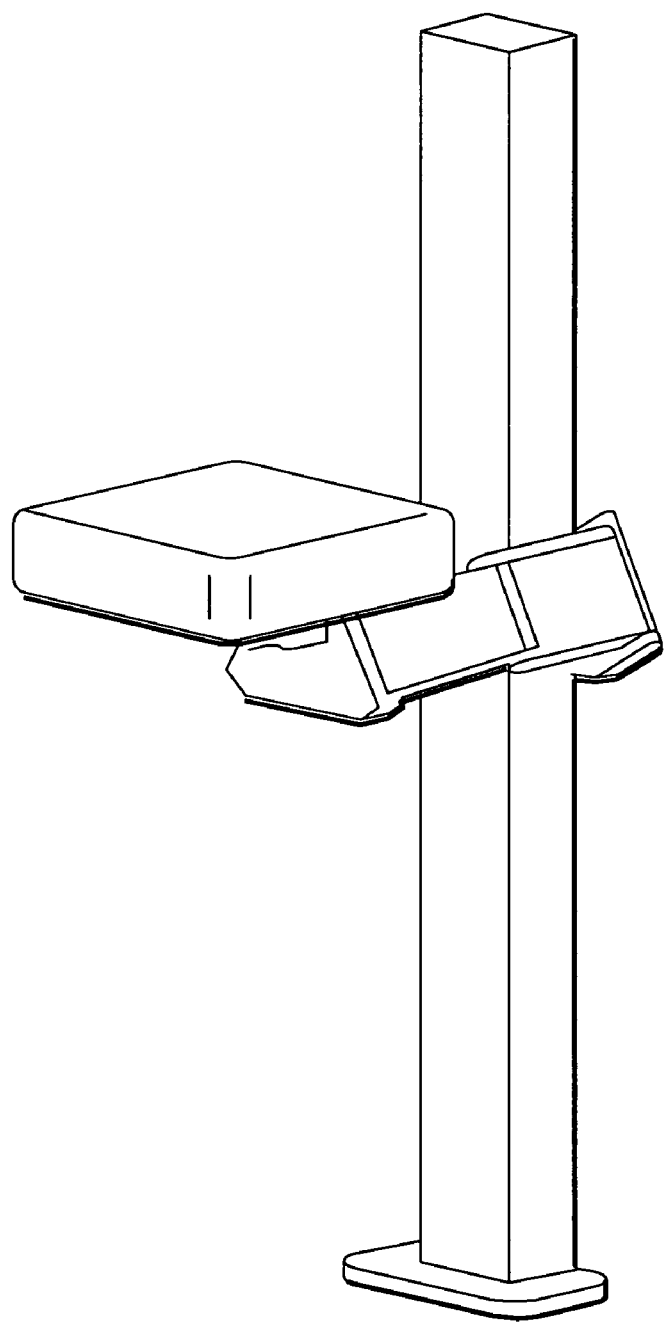
FIG. 12 shows a diagrammatic perspective view of the digital radiography apparatus wherein the bucky is in a horizontal position in the extended position.

Additionally, when bucky 16 is in the extended position, bucky 16 can be oriented horizontally, as shown in FIG. 7. As such, bucky 12 can be rotated about the x-axis. This is further illustrated in FIG. 9.

Still further, when bucky 16 is oriented horizontally, bucky 16 can be translated along the x-axis. This can be accomplished as indicated above wherein support member 12 can be mounted for translational/sliding movement in a direction substantially perpendicular to the axis of support member 12.

The movement of bucky 16 relative to support member 12 is accomplished by mounting member 14. As shown in FIGS. 2–9, mounting member 14 includes a plurality of extension arms (A1 and A2), wherein each extension arm is comprised of a plurality of extension sections joined. In the embodiments shown in FIGS. 2–9, each extension arm is comprised of two extension sections. The joints of the extension arms (and accordingly, extension sections) are disposed substantially parallel to each other.

A second embodiment of the present invention is now described with reference to FIGS. 10–21. In this second embodiment of apparatus 10, apparatus 10 includes support member 12, bucky 16, and a mounting member 24.

Figure 13:
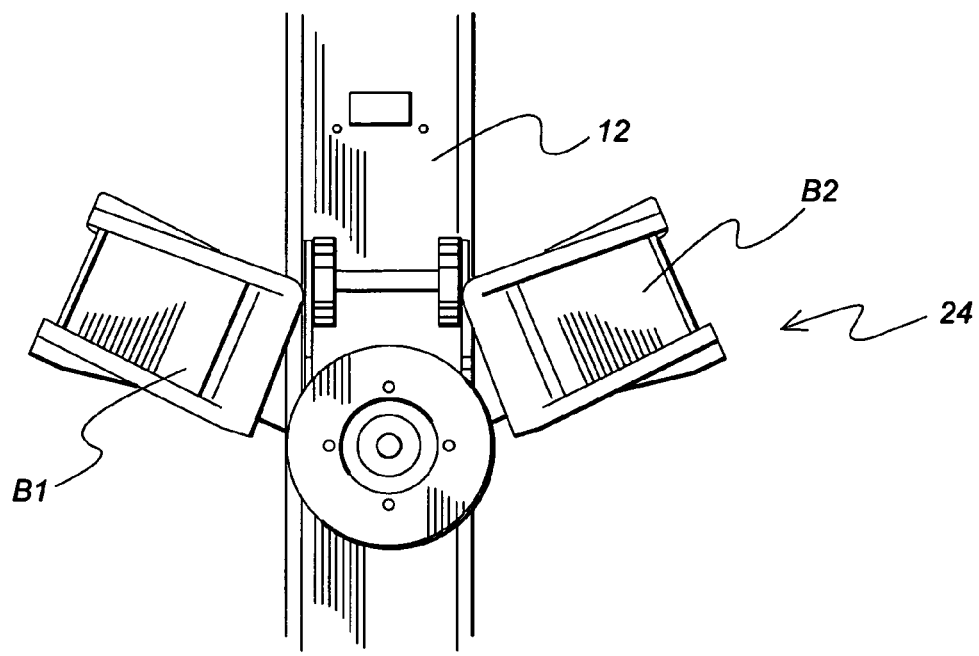
FIG. 13 shows a front view of the digital radiography apparatus.
Figure 14:
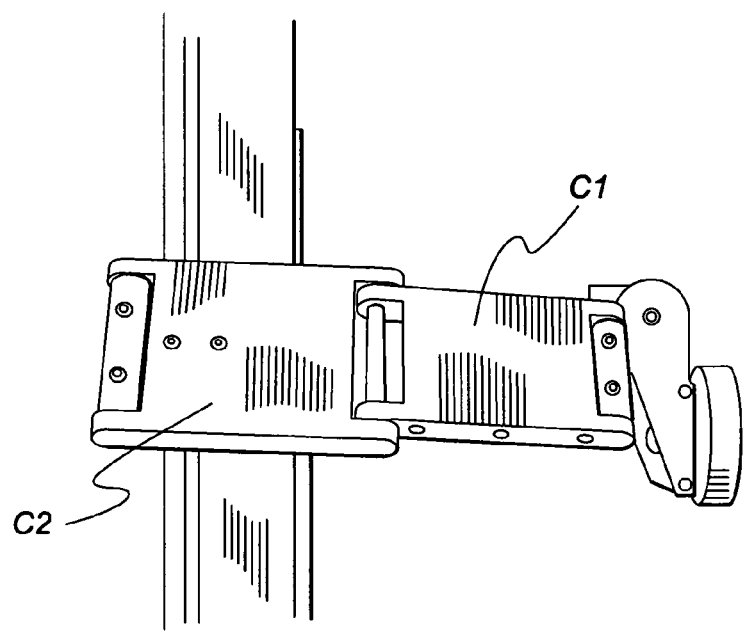
FIG. 14 shows a side view of the digital radiography apparatus wherein the bucky is in an extended position.
Figure 15:
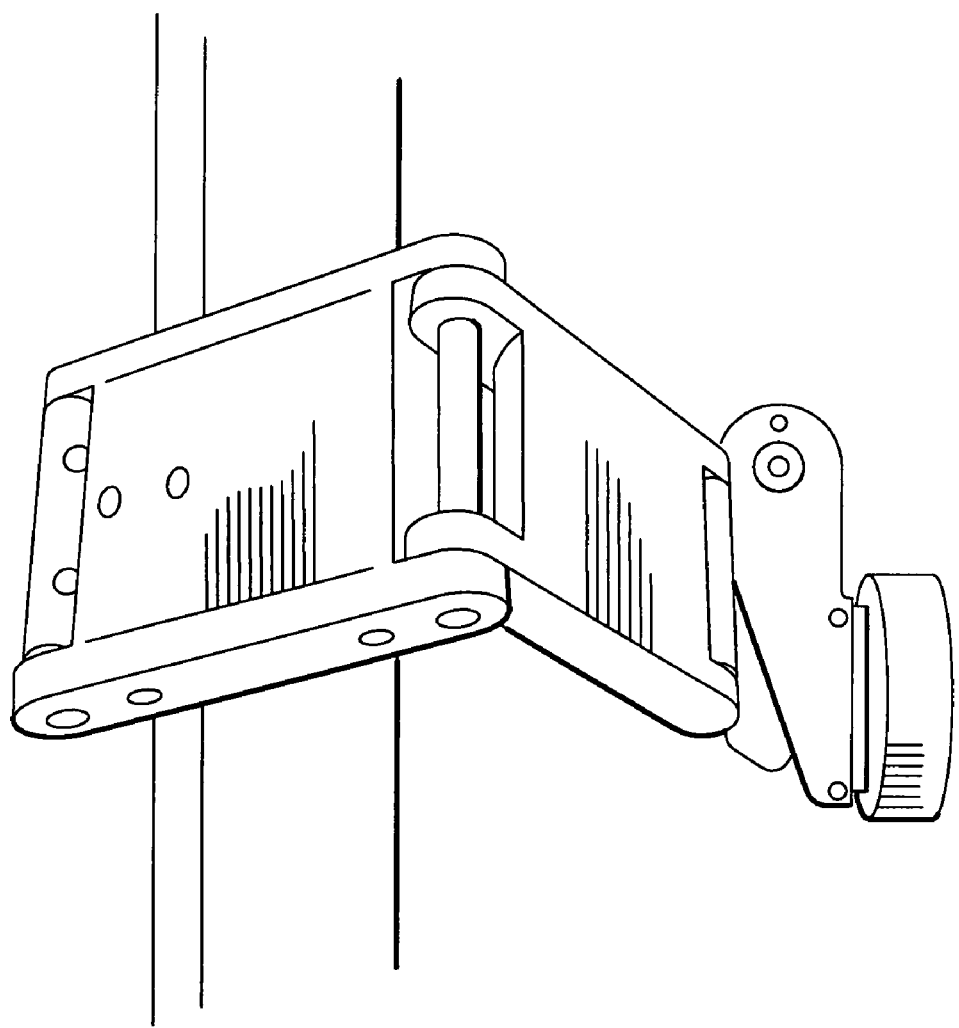
FIG. 15 shows a side view of the digital radiography apparatus wherein the bucky is in a partially extended position.
Figure 16:
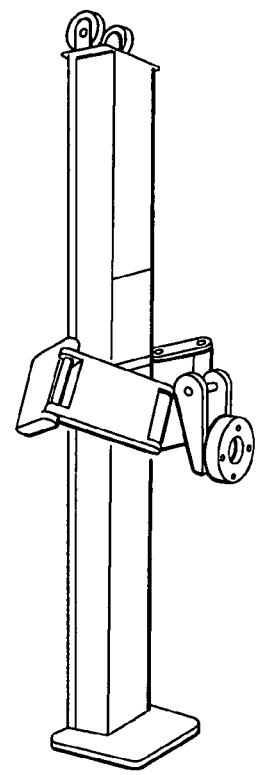
FIGS. 16 and 17 show perspective views of the digital radiography apparatus.

In this second embodiment, mounting member 24 is comprised of a plurality of extension arms, referred to as B1 and B2 in FIG. 13. Each extension arm includes a plurality of extension sections C1 and C2 that are joined at pivots.

However, in contrast to mounting member 14, the extension arms of mounting member 24 are not substantially parallel to each other. Rather, the extension arms of mounting member 24 form an included angle between the rotational axis of each arm. This included angle between the rotational axis of each arm can range from about 30 degrees to about 90 degrees (rather than the 0 degrees/parallel of mounting member). (Refer to FIG. 21)

Figure 17:
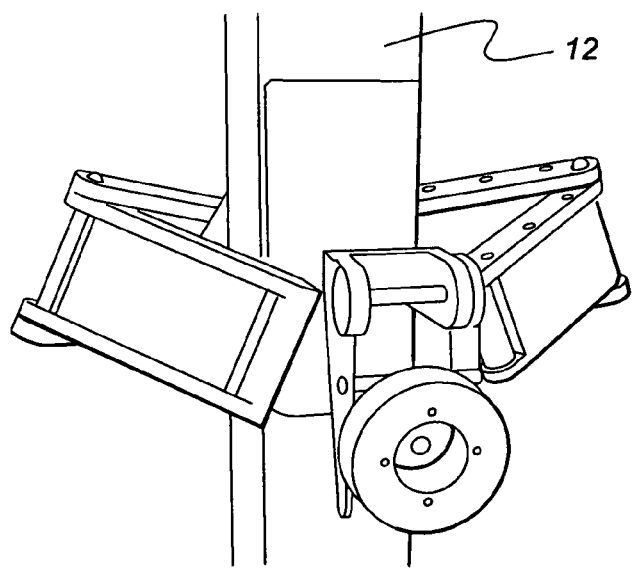
Figure 18:
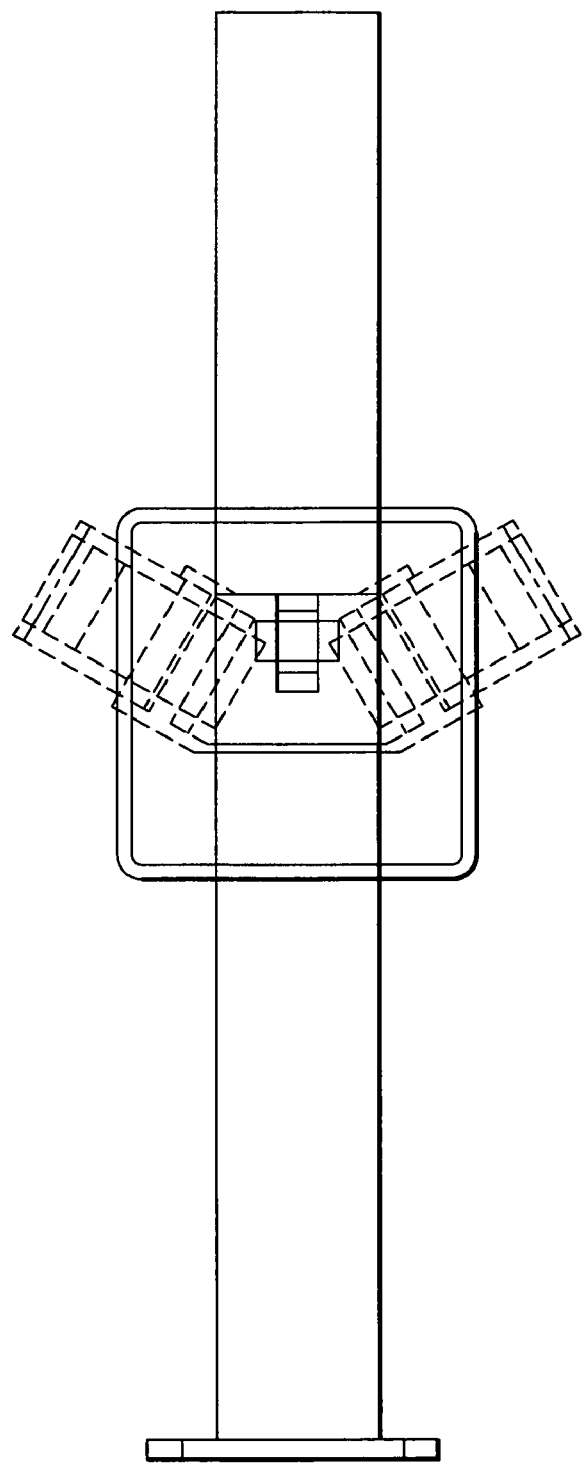
FIG. 18 shows a front view of the digital radiography apparatus.
Figure 19:
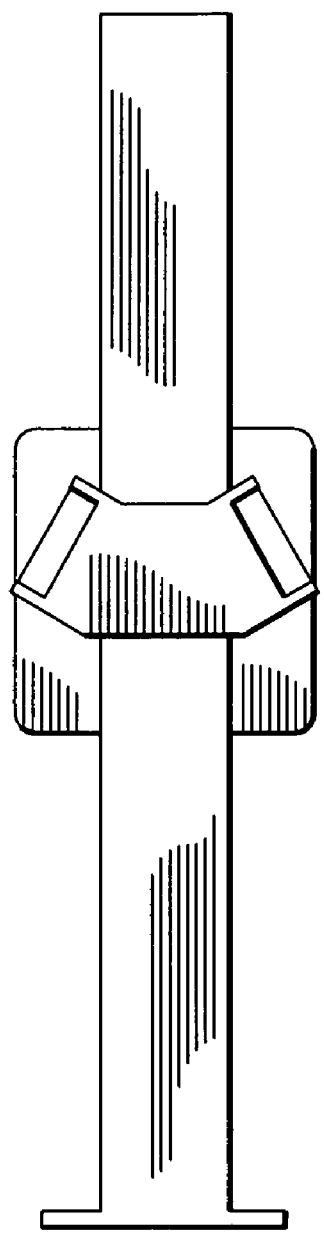
FIG. 19 shows a back view of the digital radiography apparatus.
Figure 20:
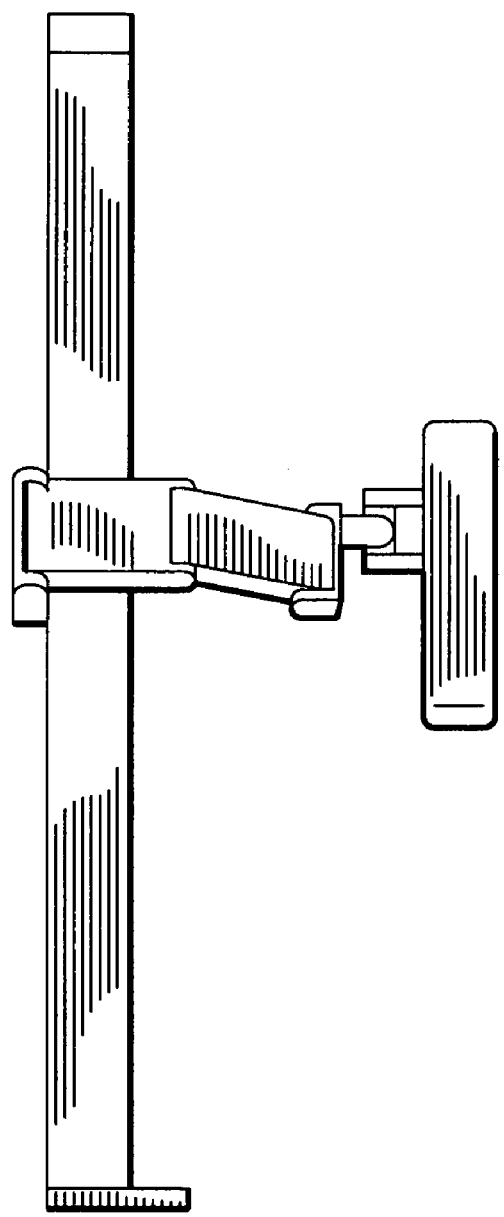
FIG. 20 shows a side view of the digital radiography apparatus.
Figure 21:
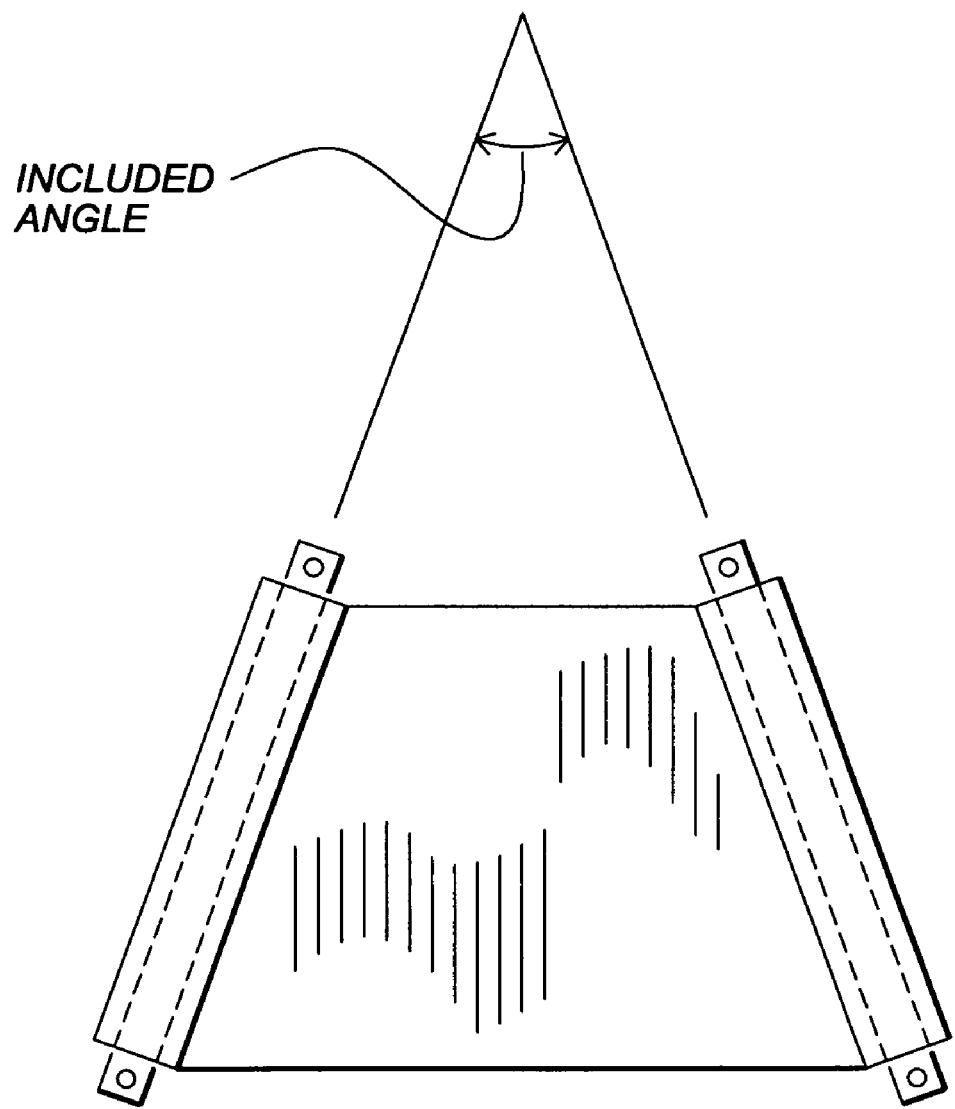
FIG. 21 shows the included angle feature of the extension arms of the digital radiography apparatus.

This angle between the rotational axis of each arm caused the arms to have a "wing" effect as shown in the figures, particularly, FIGS. 13 and 17.

This included angle, causes the planes of motion that each extension arm is constrained to, to bisect, thereby further limiting the motion of the two extension arms, to a single straight line of motion.

Applicants have found that an included angle of about 48 degrees has been found suitable for a particular application.

Within each extension arm, the plurality of extension sections are joined together for rotation motion about a rotational axis. Such motion can be accomplished by means known to those skilled in the art. Within each extension section, the rotational axes are parallel to each other, forming a first angle ANGLE1 for the first extension arm and a second angle ANGLE2 for the second extension arm. The angular difference between first angle ANGLE1 and second angle ANGLE2 is the included angle between the rotational axis of each extension arm, which, as disclosed above can range from about 30 to about 90 degrees.

An advantage of the angled extension arms (i.e., nonparallel) approach, is that a straight line extension motion is achieved without additional mechanism to keep the arm angles symmetrical. That is, the extension motion of the bucky is along a straight line, i.e., for this application, substantially perpendicular to the support member.

This is accomplished by constraining the motion between the extension sections within an extension arm and at both ends of the extension arms, to rotation in only, one parallel rotation axis. This provides a constraining motion of the extension arms to a single plane of motion freedom. For example, with two arm sections, there are three pivot axes that are parallel.

Operation of mounting member 14 and 24 to move bucky 16 can be accomplished manually by pushing/pulling/rotating the bucky.

Optionally, locks can be provided on mounting member 14,24 to lock a particular position. For example, one locking mechanism can be a magnet disposed on support member 12 which is actuated when bucky 16 is in its retracted position. To "unlock" this retracted position, the magnet could be de-activated.

Depending on the type of image being acquired by apparatus 10, a patient may desire to hug, hold, grab, apparatus 10 to maintain an imaging position. As such, the winged portion of extension arms could provide such a portion. Alternatively, handles or the like can also be provided on support member 12.

A keypad can be disposed on apparatus 10 to effect operations of apparatus 10. For example, the keypad might include locking features, controls to effect motorized translational movement of the support member, controls to effect motorized movement of the bucky on the support member, and the like.

Apparatus 10 can include an autocentering feature to affect autocentering of the apparatus. This autocentering allows a user to cause automatic movement of apparatus 10 to center apparatus 10 relative to another device which is stationary. For example, for apparatus 10, it may be desired to center apparatus 10 relative to an x-ray source. As such, a button (or other member, either on apparatus 10 or mounted elsewhere, such as on a wall or remote control device) can be actuated and apparatus 10 will move to center itself with the x-ray source. This movement can be determined by geometry and sensors disposed within the x-ray source and/or apparatus 10.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A digital radiography apparatus, comprising:
   a support member having a first axis;
   a bucky; and
   a mounting member attached to the support member and supporting the bucky to move the bucky substantially along a second axis perpendicular to the first axis between a retracted position wherein the bucky is disposed proximate the support member to an extended position wherein the bucky is not disposed proximate the support member, the mounting member including a plurality of arms, each arm having a first end attached to the support member and a second end proximate the bucky, each arm being comprised of a plurality of sections pivotally mounted to each other.

2. The apparatus of claim 1, wherein the plurality of arms form an included angle ranging from about 30 degrees to about 90 degrees.

3. The apparatus of claim 1, wherein each section within of one of the plurality of arms is disposed at the same angular orientation.

4. The apparatus of claim 3, wherein the angular orientation of the sections of one of the plurality of arms differs from the angular orientation of the sections of the other of the plurality of arms.

5. The apparatus of claim 1, further comprising means for affecting rotation of the bucky about the second axis.

6. The apparatus of claim 1, further comprising means for affecting rotation of the bucky about a third axis substantially perpendicular to the first and second axes when the bucky is in the extended position.

7. The apparatus of claim 1, further comprising means for angulating the bucky about an axis substantially parallel to the first axis when the bucky is in the extended position.

8. A digital radiography apparatus, comprising:
   a support member having a first axis;
   a bucky; and
   a mounting member attached to the support member and supporting the bucky to move the bucky substantially along a second axis perpendicular to the first axis between a retracted position wherein the bucky is disposed proximate the support member to an extended position wherein the bucky is not disposed proximate the support member, wherein the mounting member includes a plurality of arms, each arm having a first end attached to the support member and a second end proximate the bucky, and wherein each arm is comprised of a plurality of sections pivotally mounted to each other, each section within one of the plurality of arms being disposed at the same angular orientation.

9. The apparatus of claim 8, wherein the angular orientation of the sections of one of the plurality of arms differs from the angular orientation of the sections of the other of the plurality of arms.

10. The apparatus of claim 8, wherein the arms are configured for synchronized movement.

11. The apparatus of claim 8, wherein the plurality of arms form an included angle ranging from about 30 degrees to about 90 degrees.

12. The apparatus of claim 8, further comprising means for rotating the bucky about the second axis.

13. The apparatus of claim 8, further comprising means for moving the bucky between a horizontal orientation and a vertical orientation when the bucky is in the extended position.

14. The apparatus of claim 8, further comprising means for angulating the bucky about an axis substantially parallel to the first axis when the bucky is in the extended position.

* * * * *